United States Patent [19]

Moore et al.

[11] 4,307,260

[45] Dec. 22, 1981

[54] DRYING ALKYL HALIDES

[75] Inventors: Donald H. Moore, Florence, S.C.; Joel M. Leathers, Midland, Mich.

[73] Assignee: The Dow Chemical Company, Midland, Mich.

[21] Appl. No.: 100,798

[22] Filed: Dec. 6, 1979

[51] Int. Cl.³ ............................................. C07C 19/00
[52] U.S. Cl. ..................................................... 570/262
[58] Field of Search ........................... 260/652 P, 657; 570/101, 262, 258

[56] References Cited

U.S. PATENT DOCUMENTS

| | | | |
|---|---|---|---|
| 3,315,441 | 4/1967 | Hutton et al. | 55/56 |
| 3,568,409 | 3/1971 | Ferguson et al. | 55/71 |
| 4,010,017 | 3/1977 | Loyless | 260/652 P |
| 4,145,260 | 3/1979 | Steele et al. | 260/657 |
| 4,192,821 | 3/1980 | Graser et al. | 260/652 P |

*Primary Examiner*—Delbert E. Gantz
*Assistant Examiner*—Joseph A. Boska
*Attorney, Agent, or Firm*—A. C. Ancona

[57] ABSTRACT

After quenching the effluent gas from a methanol hydrochlorination reactor to condense most of the water and remove excess HCl, the wet (saturated) methyl chloride is mixed with hydrogen chloride to provide a gas mixture having a methyl chloride:HCl ratio of from about 0.4:1 to about 4:1. This mixture is then contacted with cold (−16° to −21° C.) concentrated (50 to 59%) aqeous hydrochloric acid to remove the water to a low level. Additionally an undesirable by-product, dimethylether, is removed along with the water. Alternatively the wet gas mixture may be cooled to that same temperature by passing over cooling coils, or other convenient means, to remove the water.

2 Claims, No Drawings

DRYING ALKYL HALIDES

BACKGROUND OF THE INVENTION

Alkyl halides are commonly manufactured by hydrohalogenation of alcohols. Thus, methanol and hydrogen chloride are contacted over a suitable catalyst to make methyl chloride. The hydrochlorination reaction produces an equimolar amount of water along with the desired alkyl chloride. Before the alkyl halides can be employed for most uses it is necessary to dry them. For many uses the water content must be reduced to 0.1 percent or less, even to the low parts-per-million range.

A common way of drying methyl chloride is to contact the effluent gas stream (which has had most of the water removed) with concentrated sulfuric acid. This method results in a dry methyl chloride, but the gas stream carries over some acid which is corrosive to equipment and undesirable in many reactions in which the methyl chloride is employed.

A more recent development in drying methyl chloride is described in U.S. Pat. No. 4,145,260, wherein a distillation of wet methyl chloride is conducted in the presence of hydrogen chloride to produce aqueous HCl bottoms and dry methyl chloride overhead.

In related art nitrogen trichloride and water were removed from chlorine gas by counter-current contact with aqueous hydrochloric acid (26% HCl) at 0° C. This process is described in U.S. Pat. No. 3,568,409.

Thus, it would be desirable to have a method for drying methyl chloride which would avoid the use of sulfuric acid as a drying agent.

It has now been discovered that a more convenient method of drying is to cool the gas to a temperature which condenses out substantially all of the water without condensing the methyl chloride itself.

SUMMARY OF THE INVENTION

The effluent from a methanol hydrochlorination reaction, which has had most of the water removed therefrom is mixed with hydrogen chloride and the mixture cooled to a temperature just above the condensation point of methyl chloride to remove substantially all the water. The gas stream may be cooled by contacting it with cold concentrated (50-55% HCl) hydrochloric acid e.g., by passing the gas mixture through the aqueous acid in a suitable vessel.

Alternatively, the wet gas mixture may be passed over coils containing a coolant to attain the desired temperature, or through coils immersed in a bath of coolant.

DETAILED DESCRIPTION OF THE INVENTION

A vessel, suitable for maintaining a pressure slightly above atmospheric, was fitted with a dip tube through which a gas could be bubbled into a liquid contained therein. Into this vessel was placed concentrated aqueous hydrochloric acid (ca 36% HCl) and the entire flask and contents was placed in a cooling bath. The acid was gradually cooled to −18° C. while anhydrous HCl was bubbled into the acid until a concentration of 55-59% HCl was obtained. The temperature of the aqueous acid was maintained at −18° to −20° C.

A mixture of wet methyl chloride and hydrogen chloride was then passed into the cold acid by means of the dip tube. The mixture of vapors exited through a second tube at the top of the vessel. The dry methyl chloride may then be separated by distillation from the hydrogen chloride.

The concentrated hydrochloric acid must be maintained at a concentration within the range of 55-59% by weight hydrogen chloride and at a temperature of −16° to −21° C. Both above and below those HCl concentrations the liquid hydrochloric acid will freeze at the given temperature range. At a temperature of −24° C. and below methyl chloride becomes liquid. Thus, the present process is employed under rather exacting conditions of temperature and HCl concentration.

The invention provides a method which produces a methyl chloride having less than 100 ppm water. In all of the following examples the water content is expressed as percent or parts per million by weight of the methyl chloride. Unexpectedly the undesirable by-product, dimethyl ether, is also reduced in concentration to about 1% of that originally present.

EXAMPLE 1

In the apparatus and according to the procedure described above a wet gas mixture, containing methyl chloride and hydrogen chloride in a mole ratio of 1.81/1 and 0.48% by weight water and 4000 ppm dimethyl ether (DME) both based on weight of methyl chloride, was passed through aqueous (55-59%) hydrochloric acid maintained at a temperature of about −18° C. under a pressure of about 13 psig. The exit gas stream was passed through an absorption tube containing $P_2O_5$ as absorbent to measure the water content of the gas. The water content of the methyl chloride after treatment had been reduced to 14 ppm and the DME to 40 ppm.

EXAMPLES 2-4

In the manner of Example 1, the water content of other methyl chloride-HCl gas mixtures was reduced. Conditions and results are tabularized below:

| Ex. No. | MeCl./HCl Mole Ratio | Press. Psig | Temp. °C. | $H_2O$ (ppm) In | Out | DME ppm In | Out |
|---|---|---|---|---|---|---|---|
| 2 | 0.61 | 15 | −17 | 5000 | 91 | 1100 | 10 |
| 3 | 1.17 | 14 | −17 | 4900 | 33 | 4000 | 40 |
| 4 | 2.34 | 12 | −17.5 | 4600 | 48 | 4800 | 48 |
| 5 | 1.5 | 13 | −18 | 4800 | 22 | 4000 | 40 |
| 6 | 0.42 | 12 | −16 | 4900 | 41 | 1100 | 10 |
| 7 | 0.66 | 14 | −17 | 5000 | 48 | 1100 | 10 |
| 8 | 1.0 | 13 | −17 | 4900 | 33 | 4000 | 40 |
| 9* | 3.8 | 15 | −18 | — | — | 4800 | 50 |

*Water content not measured.

EXAMPLE 10

In the alternate method coils containing a refrigerant were placed in a vessel and a wet gas mixture (MeCl/HCl) was introduced by means of a dip pipe into the bottom of the vessel, passed over the cooling coils and exited at the top of the vessel. The pressure of the gas was 14 psig, temperature in the vessel was −18° C., the mole ratio of MeCl/HCl was 1.81/1 and the water content of the methyl chloride was 0.75%. The exiting methyl chloride contained 41 ppm $H_2O$ by weight.

While the second method is an operable method, the first is preferred from economic considerations. Regardless of which method is used the operable mole ratio of the MeCl/HCl mixture is about 0.4/1 to about 4/1. The preferred molar ratio is 1/1 to 3/1. Operable pressure is from about 5 to 20 psig., although 12-15 psig is preferred. The temperature of operability is critical because of the potential condensation of methyl chloride and of the freezing of the aqueous HCl solution. Thus a range of about −16° to about −21° C. is a limitation for the present invention.

The present invention, then, is a means of drying methyl chloride and mixtures of methyl chloride and hydrogen chloride by cooling a gaseous methyl chloride/hydrogen chloride mixture, having a mole ratio of about 0.4/1 to about 4/1, to a temperature within the range of about −16° to about −21° C. at a pressure within the range of about 5 to 20 psig. The preferred method of cooling is to contact the mixture with concentrated aqueous hydrochloric acid (50–59% HCl). Alternate, but less preferred, method is to cool the gas mixture by passing over refrigerated coils.

We claim:

1. A method for drying a gaseous mixture of hydrogen chloride and methyl chloride which comprises cooling said mixture to a temperature of −16° to −21° C. by contacting with cold aqueous hydrochloric acid containing 55–59% HCl to dry said mixture.

2. The method of claim 1 wherein the pressure is maintained within the range of 5–20 psig.

* * * * *